United States Patent [19]

Gole et al.

[11] Patent Number: 5,330,764

[45] Date of Patent: Jul. 19, 1994

[54] METHODS OF PREPARING BULK DELIVERY MATRICES BY SOLID-STATE DISSOLUTION

[75] Inventors: Dilip J. Gole, Ann Arbor; R. Saul Levinson, Saline; James Carbone, Belleville; J. Desmond Davies, Grosse Pointe Farms, all of Mich.

[73] Assignee: Janssen Pharmaceutica Inc., Piscataway, N.J.

[21] Appl. No.: 734,635

[22] Filed: Jul. 23, 1991

Related U.S. Application Data

[63] Continuation of Ser. No. 613,087, Nov. 6, 1990, Pat. No. 5,215,756, which is a continuation-in-part of Ser. No. 454,938, Dec. 22, 1989, abandoned.

[51] Int. Cl.$^5$ .............................. A61K 9/14
[52] U.S. Cl. .................... 424/484; 424/422; 424/485
[58] Field of Search ............. 424/484, 485, 422; 34/15

[56] References Cited

U.S. PATENT DOCUMENTS

| | | | |
|---|---|---|---|
| 3,285,025 | 10/1966 | Shaul | 426/384 |
| 3,402,047 | 9/1968 | Shaul | 426/384 |
| 3,873,745 | 3/1975 | Key | 426/385 |
| 4,205,132 | 5/1980 | Sandine | 426/385 |
| 4,328,218 | 5/1982 | Sotomura | 424/123 |
| 4,329,281 | 5/1982 | Christiansen | 424/88 |
| 4,371,516 | 2/1983 | Gregory | 424/485 |
| 4,477,452 | 10/1984 | Haeger | 514/196 |
| 4,496,684 | 8/1990 | Blank et al. | 424/441 |
| 4,547,462 | 10/1985 | Tamai | 424/118 |
| 4,642,903 | 2/1987 | Davies | 34/15 |
| 4,758,598 | 7/1988 | Gregory | 424/484 |
| 4,812,445 | 3/1989 | Eden | 424/484 |
| 4,840,796 | 6/1989 | Sweet | 424/484 |
| 4,851,392 | 7/1989 | Shaw | 514/948 |
| 4,882,154 | 11/1989 | Yang | 514/948 |
| 4,920,132 | 4/1992 | Huang | 514/314 |
| 4,940,588 | 7/1990 | Sparks | 424/484 |
| 4,994,273 | 2/1991 | Zentner | 424/422 |
| 5,039,540 | 8/1991 | Ecanow | 426/385 |
| 5,079,018 | 1/1992 | Ecanow | 426/385 |

FOREIGN PATENT DOCUMENTS

| | | |
|---|---|---|
| 0394050 | 4/1990 | European Pat. Off. . |
| 0689767 | 6/1951 | United Kingdom . |
| 2114440B | 7/1985 | United Kingdom . |

OTHER PUBLICATIONS

Kawia, Introduction ot Organic Laboratory Technique (1976), pp. 508-509; 514-516.

Primary Examiner—Thurman K. Page
Assistant Examiner—William E. Benston, Jr.
Attorney, Agent, or Firm—Allegretti & Witcoff, Ltd.

[57] ABSTRACT

A method is disclosed for preparing pharmaceutical and other matrix systems that comprises solidifying a matrix composition dissolved or dispersed in a first solvent and subsequently contacting the solidified matrix with a second solvent that is substantially miscible with the first solvent at a temperature lower than the solidification point of the first solvent, the matrix components being substantially insoluble in the second solvent, whereby the first solvent is substantially removed resulting in a usable matrix.

15 Claims, No Drawings

METHODS OF PREPARING BULK DELIVERY MATRICES BY SOLID-STATE DISSOLUTION

This application is a continuation of copending U.S. patent application Ser. No. 07/613,087, filed Nov. 6, 1990 now U.S. Pat. No. 5,215,756, the entirety of which is incorporated herein, which is a continuation-in-part of copending U.S. patent application Ser. No. 07/454,938, filed Dec. 22, 1989, abandoned, the entirety of which is incorporated herein by reference.

BACKGROUND OF THE INVENTION

1. Field of the Invention

The present invention relates to methods for preparing products by removal of a solid frozen solvent from a frozen matrix mixture.

2. Description of the Background Art

Freeze-drying, i.e., lyophilization, is a well known method of drying heat-sensitive materials in order to protect them from thermal damage. In the past, preparations containing active ingredients, such as pharmaceuticals, nutrients, diagnostics, fertilizers and insecticides, have been prepared by freeze-drying aqueous solutions or suspensions containing these bioactive ingredients. Conventional methods of freeze-drying or lyophilization involve the freezing of a material at a very low temperature followed by a dehydration by sublimation under high vacuum. These conventional techniques generally employ expensive, bulky and specially designed lyophilization equipment.

One problem that has arisen, however, with the use of conventional freeze-drying processes is cracking of the freeze-dried preparations. Typically, cracking is caused by the stresses set up during ice crystallization. Though cracking is never desirable, it is especially undesirable where drop methods of freezing are employed. In such cases, cracking of the frozen droplets usually results in unusable and inelegant remnants of fractured droplets.

Another problem encountered by use of known freeze-drying methods is a phenomenon called meltback. Meltback occurs when the heat required during the drying process melts the frozen material. As such, meltback defeats the whole purpose of freeze-drying-the removal of water through sublimation as opposed to evaporation. To avoid meltback in conventional freeze-drying methods, only limited amounts of material of limited thickness can be dried at one time or, alternatively, very low temperatures have to be used, thereby considerably extending the time required for sublimation. Even with these limitations, conventional freeze-drying methods are not always sufficient to prevent meltback.

Yet another problem inherent in conventional freeze-drying methods is a lack of resistance to disintegration in freeze-dried materials, i.e., they have little strength. Freeze-drying methods generally yield products that merely crumble when handled. Various freeze-drying and packaging methods have been employed in attempts to circumvent this problem. For example, U.S. Pat. No. 4,305,502 describes a method for forming a shaped article by a lyophilization process in a depression in a sheet of film material. However, such packaging techniques do not avoid the problems posed by conventional freeze-drying methods; the tablets are still susceptible to crumbling if transferred to other packaging.

In the area of pharmaceuticals, known freeze-dried dosage forms do not always exhibit fast dissolution rates when brought into contact with appropriate solvents, such as water, saliva or gastrointestinal fluids. Rapid dissolution of pharmaceutical dosage forms can be of critical importance in instances where it is desirable that the pharmaceutical enter the physiological system as soon as possible.

For example, many individuals, particularly pediatric and geriatric patients, experience difficulty and discomfort in swallowing solid, slow dissolving tablets and capsules. Similar difficulties are encountered when administering pharmaceuticals orally to animals in the veterinary treatment of those animals.

Various methods for freeze-drying pharmaceutical dosage forms by lyophilization have been developed to provide fast dissolving dosage forms. U.S. Pat. Nos. 2,166,074; 3,234,091; 4,371,516 and 4,302,502 and United Kingdom Patents No. 698,767 and 1,310,824 are all concerned with freeze-dried dosage forms that are able to dissolve rapidly. In addition, Davies, in U.S. Pat. No. 4,642,093, teaches a procedure for preparing a freeze-dried (lyophilized) foam dosage form using conventional lyophilization techniques that results in rapidly dissolving pharmaceutical dosage forms.

Yet another problem intrinsic to conventional lyophilization methods is the lack of uniform porosity in the lyophilized product. Uniform porosity in a lyophilized product is critical for post-loading a dosage form with an active agent.

Thus, there is a need for a method of producing a dosage form similar to that produced by lyophilization that will avoid cracking and meltback. Furthermore, there is a need for methods of producing pharmaceutical dosage forms having adequate strength, porosity and exhibiting a fast speed of dissolution upon ingestion.

SUMMARY OF THE INVENTION

It is an object of the present invention to provide an inexpensive method of removing solid solvent from a solidified mixture that prevents or reduces the incidence of cracking of the final preparation.

It is an additional object of the present invention to provide a method of removing solid solvent from a solidified mixture wherein the incidence of meltback during the process is reduced or eliminated.

It is a further object of the present invention to provide a method of removing solid solvent from solidified pharmaceutical mixtures so that the prepared dosage forms exhibit rapid dissolution in appropriate solvents.

It is another object of the present invention to provide a method of preparing a dosage form having uniform porosity.

It is a further additional object of the present invention to provide dosage forms that include active ingredients, such as pharmaceuticals, nutrients, diagnostics, confectioneries, fertilizers and insecticides.

It is yet another object of the present invention to provide a method of preparing a dossage form having adequate strength for handling.

It is a specific object of the present invention to provide a solid-state dissolution method of removing solid solvent from solidified samples. According to the inventive method, one or more delivery matrix forming agents (and optionally a sample to be delivered) are dissolved or dispersed in a first solvent, solidified and subsequently contacted with a second solvent at a temperature at or higher than the solidification point of the second solvent and at a temperature at or lower than the solidification point of the first solvent. The first solvent in the solidified state is substantially miscible with the second solvent, while the matrix forming agent(s) (and sample if present) are substantially insoluble in the second solvent. The first solvent is thereby substantially removed from the solidified matrix yielding a solid matrix (optionally containing the sample) substantially free of the first solvent.

It is an additional specific object of the present invention to provide a solid-state dissolution method for preparing unit dosage forms wherein a first solvent is removed from the dosage form while it is still in the solid state. According to this inventive method, one or more matrix forming agents (and optionally a sample to be delivered) are dispersed or dissolved in a first solvent and a unit volume of the solution or dispersion is then solidified. The solidified unit volume of sample is next contacted with a second solvent, which is substantially miscible with the first solvent in the solidified state. The second solvent is at a temperature at or higher than the solidification point of the second solvent and at a temperature at or lower than the solidification point of the first solvent, the matrix forming agent (and sample if present) being substantially insoluble in the second solvent. Thus, the first solvent is substantially removed from the solidified unit volume yielding a dosage form unit (containing a unit dosage amount of the sample if present) that is substantially free of the first solvent. In one alternative, the processed dosage form may be contacted with a bioactive agent to yield a dosage form having a specific amount of the bioactive agent dispersed therethrough.

It is a further object of the present invention to provide a solid carrier system for chemicals that a user may add to a medium to instantaneously obtain a solution or dispersion of desired concentration.

The method of the present invention produces dried samples with minimal cracking or meltback of the processed sample.

The resulting preparations exhibit uniform high porosity while having sufficient strength, i.e., resistance to disintegration or crumbling under normal manufacturing and handling conditions.

It is another object of the present invention to provide improved dosage forms containing amino acids having from 2 to 12 carbon atoms as matrix forming agents. In a particularly preferred embodiment, glycine forms a primary part of the matrix of the porous dosage form. This aspect of the present invention provides improved dosage forms having the following advantages: quick dissolution and disintegration, pleasant taste and mouthfeel, nutrional value, low calorie content and noncariogenicity.

In the realm of pharmaceutical use, pharmaceutical dosage forms prepared according to the present invention exhibit rapid dissolution upon contact with physiological solvents, such as water, saliva, or gastrointestinal fluids. Therefore, the present inventive pharmaceutical dosage forms provide a more rapid dispersion of the pharmaceutical within the body upon ingestion.

Embodiments of the present invention have the following potential applications:

PHARMACEUTICAL

1. Dosage forms having mucoadhesive properties.
2. Dosage forms designed to deliver drug at a controlled rate.
3. Dosing units designed to deliver drugs in the eye.
4. Dosing units designed to deliver drugs in vaginal, rectal and other body orifices.
5. Solid dosage forms designed to replace liquid formulations.
6. Dry medicated preparations for topical application after resolution (reconstitution).
7. Preparation of medicated units or sheets for topical application.
8. Preparation of more palatable dosage forms of drugs that exhibit disagreeable organoleptic properties.
9. Dosage forms for oral delivery of drugs to persons who have difficulty swallowing tablets or capsules.

FOOD

1. Preparation of and presentation of dried products composed of food materials.
2. To provide a method for the selective extraction of a material in the solid form during the drying process.
3. Preparation of confectionery products.
4. Preparation of dosing units for the purpose of modifying properties (e.g. taste, color etc.) or quality of drinking water.

VETERINARY

1. Preparation of dosing units for veterinary use.
2. Preparation of aquarium care and feed products.

COSMETICS

1. Preparation of dry systems for medical and cosmetic use after resolution.

DIAGNOSTIC

1. Enzyme/cofactors and biochemical carrier systems.

SANITARY

1. Preparation of dosing units for water purification.
2. Preparation of fragrance carrier units for personal, household and industrial use.

OTHER

1. Reconstitutable carrier units for pigmented application for paint and other artistic uses.
2. Agriculture and horticulture products requiring release of active ingredients in the presence of water or rain.
3. Preparation of easily removable mold or model material.
4. Preparation of easily removable space maintenance and/or alignment aid for construction or manufacturing.

Further objects and embodiments of the present invention will be made known in the following description of the preferred embodiments and claims. Though the following description of the preferred embodiments focuses on the inclusion of pharmaceuticals as the active agents, it is to be understood that the desirable properties of the inventive methods and dosage forms may be advantageously used in connection with many different types of active agents.

DESCRIPTION OF THE PREFERRED EMBODIMENTS

The inventive solid-state dissolution method for preparing delivery matrices and dosage forms begins with a mixture of at least one matrix forming agent in a first solvent. This mixture may be aqueous in nature and may contain various chemicals, drugs and adjuvants in a suitable first solvent. The resulting mixture is cooled at a controlled rate until completely solidified, and subsequently immersed into a suitable second solvent at a temperature below the melting point of the first solvent. The solidified first solvent substantially dissolves into the second solvent and produces a solid product essentially free of the first solvent as a matrix and any chemicals or drugs present in the original mixture. Residual second solvent may be evaporated subsequent to removing the matrices from the second solvent bath. Alternatively, residual second solvent may be removed by contacting the sample with one or more additional solvents having greater volatility than the second solvent.

The various ingredients that may be incorporated into the initial mixture may include matrix forming agents and secondary components. Matrix forming agents suitable for use in the present invention include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other matrix forming agents suitable for use in the present invention include sugars such as mannitol, dextrose, lactose, and galactose; cyclic sugars such as cyclodextrin; inorganic salts such as sodium phosphate, sodium chloride and aluminum silicates; and amino acids having from 2 to 12 carbon atoms such as glycine and 1-alanine. Persons having skill in the art will recognize other acceptable matrix forming agents that may be employed in the present invention.

One or more matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion of any active ingredient within the solution or suspension. This is especially helpful in the case of active agents that are not sufficiently soluble in water and must, therefore, be suspended rather than dissolved.

Secondary components such as preservatives, flavors, antioxidants, surfactants, sweeteners, or colorings may also be incorporated in the formulation. Other secondary components include the active or bioactive agents to be dosed or delivered. These active agents may include pharmaceuticals, nutrients, vitamins, minerals, diagnostics, fertilizers and insecticides. Examples of pharmaceutical agents that may be incorporated in the initial mixture are chlorpheniramine maleate, pseudoephedrine, dextromethorphan, meclizine dihydrochloride, haloperidol, albuterol sulfate, dimenhydrinate, and benzodiazepines such as diazepam, lorazepam and congeners thereof. However, virtually any pharmaceutical agent may be used in connection with the present invention, either by adding the pharmaceutical to the mixture to be solidified or by post loading the pharmaceutical onto a preformed placebo delivery matrix or dosage form.

The speed in which the sample prepared by the inventive method dissolves is dependent in large part on the choice of matrix forming agent(s) and their concentration. Compounds (either alone or in combinations that can be used as a matrix forming material for producing placebos or matrices are as follows:

1. Hydroxyethylcellulose
2. Sodium carboxymethylcellulose
3. Microcrystalline cellulose
4. Corn syrup solids
5. Maltrins (maltodextrins)
6. Polydextroses
7. Pectins
8. Carrageenan
9. Agar
10. Chitosan
11. Locust bean gum
12. Xanthan gum
13. Tragacanth
14. Guar gum
15. Konjac flour
16. Rice flour
17. Wheat gluten
18. Sodium starch glycolate
19. Gelatin (pharmaceutical or food grade)
20. Soy fiber protein
21. Potato protein
22. Papain
23. Horse radish peroxidase
24. Glycine
25. Mannitol.

Preferred matrix forming agents include pharmaceutical grade gelatins, pectins (nonhydrolyzed, partially hydrolyzed or hydrolyzed), glycine and mannitol, either alone or in combination. Various concentrations of matrix forming agents may be used in the present invention. Preferred concentrations of matrix forming agents in a suitable solvents are about 0.1 to 15% weight/weight (w/w). A more preferred concentration is about 0.5 to 4% (w/w). Optimum results are obtained from the present inventive method in pharmaceutical applications when an approximately 2% weight/weight aqueous solution of the matrix forming agent(s) is used.

The concentrations of secondary components incorporated in the initial mixture are limited primarily by the solubility of the secondary component(s) in the solvent used to dissolve the component. The concentration required is defined by the amount of agent to be incorporated in the dosage form. Therefore, concentrations of these components in the initial mixtures may range from about 0.0001 to 20%.

Various solvents may be employed in the present invention. A first solvent must be chosen that will dissolve and/or disperse the matrix forming agents, and other miscellaneous agents of the sample. Furthermore, the first solvent must be such that it has a solidification point higher than the solidification point of the second solvent. A preferred first solvent in water; other suitable first solvents include polyethylene glycols, carboxypolymethylenes, tert-butyl alcohol, acetonitrile, acetamide and phenol. A first solvent may comprise a suitable combination of any of these solvents, such as, for example, a water:tert-butyl alcohol solvent mixture.

The second solvent should desirably act as a solvent for the solidified first solvent. It is advantageous that the dissolution solvent also have a solidification point below the solidification point of the first solvent. When a substantially dry sample, placebo or dosage form is desired, it is advantageous that the second solvent have a relatively low boiling point or relatively high vapor pressure such that the second solvent evaporates quickly from the processed sample. Therefore, preferred second solvents will have boiling points or vapor pressures such that the solvent evaporates readily at atmospheric pressure or at reduced pressure. Preferred second solvents for use with water as the first solvent include materials which are water miscible. These materials may be used in the solid, liquid or gaseous state.

However, those skilled in the art will appreciate that various solid sample formulations may be desired that are not dry but have substantial amounts of liquid dispersed throughout. Hence, a solvent having a relatively high boiling point such as, for example, dimethylformamide or ethylene glycol, could be employed as the second solvent.

It is advantageous that the dosage form components (matrix forming agents and secondary components) be substantially insoluble in the second solvent, i.e., the second solvent will not dissolve the sample components. Hence, depending on these components, acceptable second solvents include methanol, ethanol, acetone, water, isopropyl alcohol, methyl isobutyl ketone and liquid carbon dioxide. Various mixtures of these solvents may comprise the second solvent of the present invention.

Various combinations of first solvent:second solvent may be employed in the present invention. A preferred first solvent:second solvent system for pharmaceutical purposes is water:absolute ethanol. Other systems may be chosen based on the sample components to be processed. Therefore, other suitable first solvent:second solvent systems include tert-butyl alcohol:water; acetamide:methanol; phenol:isobutyl ketone and polyethylene glycol:alcohol, among others.

The mixtures of sample components to be solidified may be in a variety of forms. They may be solutions, suspensions, dispersions, emulsions, or foams. Persons having skill in the art will recognize acceptable methods for preparing each of these. A foam sample may be prepared by dispersing a gas in a liquid. A preferred method for preparing such a foam is described by Davies in U.S. Pat. No. 4,642,903, the entirety of which is incorporated herein by reference.

The mixture may be solidified by any conventional cooling process. For example, the mixture may be solidified by dispensing it into preformed molds and subsequently cooling such molds on refrigerated shelves or in refrigerated chambers. Alternatively, the molds containing the mixture may be passed through a stream of cold gas or vapor, such as liquid nitrogen in a freezing tunnel. A preferred method for solidifying the mixtures in the molds is to surround the molds in dry ice until the mixture has solidified.

As an alternative to the use of molds, the mixtures may be solidified in dropwise fashion. For example, the mixture may be pumped or fed under gravity through an orifice in order to form drops, spheres or a spray of small particles. These drops can then be solidified by passage through a cold gas or liquid, for example, liquid nitrogen or liquid nitrogen vapor. Another possibility is that drops of the mixture may be solidified in a chilled liquid that is immiscible with the mixture. In such cases, the relative densities of the liquid and the mixture are controlled such that the drops can either pass through the chilled immiscible liquid as they solidify or, alternatively, the solidified droplets may float on the surface of the chilled immiscible liquid. This latter flotation feature facilitates the collection of the solidified droplets. An example of a liquid that may be chilled and that is immiscible with most primarily aqueous mixtures is trichloroethylene.

The resulting solidified mixture is contacted in the second solvent whereby the solidified first solvent dissolves into the second solvent. The contact time depends upon the amount of first solvent to be dissolved from the solidified mixture. This in turn is related to the size of the solidified mixture. The time required is further related to the temperature of the second solvent.

It is advantageous that the second solvent be at a temperature lower than the solidification point of the first solvent. For applications using a water:ethanol system the temperature of the second solvent may be about 0° to −100° C. A preferred temperature for this system is about −4° to −20° C.

In other systems, it is preferred that the second solvent be at a temperature of about 1° to 100° C. below the solidification point of the first solvent. A more preferred temperature for the second solvent is about 4° to 20° C. below the solidification point of the first solvent. At these temperatures, the amount of second solvent required to dissolve first solvent should be about 2 to 40 times the total weight of delivery matrices or dosage forms to be processed.

A preferred weight of second solvent for use at a temperature of about 10° to 20° C. below the melting point of the first solvent is about 4 to 6 times the total weight of the dosage form or matrix to be processed.

A preferred amount of ethanol for use at −4° to −20° C. is about 20 times the weight of samples to be processed. For example, to process 40 1 ml matrices, about 800 gm of ethanol would be used. When these preferred temperatures and weights of second solvent are employed, the contact times of matrix with second solvent are about 1 to 20 hours. A contact time of about 2 to 10 hours is preferred for a water:ethanol system. For large sizes, longer contact times are necessary. These preferred contact times and temperatures afford maximum strength and porosity of the processed formulation.

Various methods exist for contacting the frozen dosage unit/matrix with the second solvent. These include immersing the formulation into a solvent bath and spraying the formulation with the solvent. A preferred method of contacting the solidified mixture with the second solvent is immersion.

Intimate contact of the second solvent with the dosage form can be assured by continuous or intermittent mixing of the second solvent with the sample or pumping of the second solvent through a vessel containing the sample with or without recirculation of the second solvent. Alternatively, microwave assistance may be used to facilitate dissolution of the first solvent.

Removal of the resulting processed sample or product from the second solvent yields a sample or dosage form having uniform porosity and high resistance to crumbling. The product or formulation may be immediately used, packaged, or stored.

Alternatively, any residual second solvent may be removed by placing the product in a vacuum chamber under reduced pressure, exposing a volatile second solvent to the atmosphere at normal or elevated temperatures, or passing a stream of air or nitrogen over the sample at normal or elevated temperatures with our without recirculation. Alternatively, microwave assisted drying may be used.

In another embodiment, the product may be contacted with a third solvent to remove any residual second solvent. It is advantageous that the third solvent is a solvent having greater volatility than the second solvent such that it will readily evaporate from the product. This third solvent advantageously will be substantially immiscible with the product constituents.

Formulations containing an active agent such as a chemical or drug that is insoluble in the second or dissolution solvent may be prepared by directly adding the agent to the dispersion or solution to be solidified. However, active agents that are substantially soluble in the second solvent should desirably not be added to the initial mixture because some portion of this chemical or drug may be lost to the second solvent upon dissolution of the first solvent into the second solvent. Therefore, dosage forms or matrices having such chemicals or drugs may be advantageously prepared by first preparing a placebo or blank dosage form and subsequently contacting that dosage form with a specific amount of the active agent in a unit volume of a suitable solvent. These active agents may be loaded or dosed on the placebo as a solution, suspension, dispersion or emulsion of the agent in a carrier solvent immiscible with the placebo materials. Thus, the active agent will be substantially distributed throughout the placebo.

The carrier solvent is then allowed to evaporate at normal pressure and normal or elevated temperatures, by passing a stream of air or nitrogen over the dosage form at normal or elevated temperatures, or by placing the dosage form in a vacuum chamber under reduced pressure and normal or elevated temperatures. Alternatively, microwave assisted drying may be used. Alternatively, the dosage form may be placed in a vacuum chamber to remove the residual carrier solvent.

The active agents that may be post loaded on the placebo or blank include the secondary components that may be added to the initial mixture to be processed. The concentration of these agents in the post loading solution is defined by the amount of agent desired in the final processed dosage forms. These concentrations are only limited by the solubility of the agent in the post loading solvent, although the use of serial post loading and/or suspensions can overcome most solubility limitations. Accordingly, the concentration of the active agent may range from about 0.0001% to 20% or more.

The concentration of active agent in the final dosage form prepared by either method, i.e., post loading or conventional premixing, it related to the amount of active agent desired to be delivered in the processed dosage form. This concentration is limited by the solubility of the active agent in the solvent, although dosage forms may be serially processed with multiple post loadings in order to increase the concentration to a desirable level. In addition, suspensions of the agent(s) may be used to post load the placebo. Accordingly, the concentration of active agent in the final matrix or dosage form may range from less than 0.01% to more than 300% of the weight of the dosage form.

Dosage forms may be prepared in a wide variety of sizes through use of the present invention, ranging from about 0.25 ml to 30 ml and larger. Large dosage forms may be advantageously prepared by the present invention without the long drying times required by lyophilization.

In another preferred embodiment of the present invention, one or more small amino acids having from 2 to 12 carbon atoms are used as a matrix forming agent. Glycine and 1-alanine are the particularly preferred amino acids for this purpose. The amino acid(s) should preferably be present in concentrations of about 0.1% to 100% (w/w) of the total solids content in the initial solution and/or concentrations of about 0.1% to 100% (w/w) of the total solids content in the final dosage form. Embodiments containing glycine or other small amino acids may be processed by the solid-state dissolution procedures disclosed herein or by conventional lyophilization techniques well known to those of skill in the art. The resulting dosage forms have a porous network of matrix material and rapidly disintegrate in water in less than about 10 seconds. Active agents may be incorporated into these dosage forms by the methods disclosed herein.

The invention is illustrated further by the following examples, which are not to be construed as limiting the invention in scope or spirit to the specific procedures described in them.

EXAMPLE 1

Preparation of a Placebo Carrier Matrix By Solid-State Dissolution

Gelatin (pharmaceutical grade) (20 g) and mannitol (30 g) were dissolved in 950 g of water with heating and constant stirring. The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at $-15°$ C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 2

Preparation of a Placebo Carrier Matrix By Solid-State Dissolution

Gelatin (pharmaceutical grade) (20 g) and mannitol (30 g) were dissolved in 950 g of water with heating and constant stirring. The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were then weighed and immersed into 5000 g of methanol at $-15°$ C. Each frozen sample weighed 1.0 g. When all the ice was dissolved into the methanol the product was transferred to a vacuum chamber in order to remove residual methanol. This produced a sample, i.e., a network of carrier material, that disintegrated rapidly in 1 to 5 seconds when taken orally. Each resulting processed placebo weighed 50 mg.

EXAMPLE 3

Preparation of a Placebo Carrier Matrix By Solid-State Dissolution

Gelatin (pharmaceutical grade) (20 g) and mannitol (30 g) were dissolved in 950 g of water with heating and constant stirring. The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were then weighed and immersed into 5000 g of acetone at −15° C. Each frozen sample weighed 1.0 g. When all the ice was dissolved into the acetone the product was transferred to a vacuum chamber in order to remove residual acetone. This produced a sample, i.e., a network of carrier material, that disintegrated rapidly in 1 to 5 seconds when taken orally. Each of the processed samples weighed 50 mg.

EXAMPLE 4

Preparation of a Placebo Carrier Matrix Containing a Sweetener

Gelatin (pharmaceutical grade) (20 g), mannitol (30 g), and aspartame (20 g) were dissolved in 930 g water with heating and constant stirring. The resulting solution was transferred accurately into 1 ml size molds. Placebo samples were prepared using the method described above in Example 1. This produced a network of the carrier material and aspartame that disintegrated rapidly, in 1 to 5 seconds, when taken orally. Each of the processed aspartame containing samples weighed 70 mg.

EXAMPLE 5

Preparation of a Pharmaceutical Dosage Form by Post-Loading the Active Agents

A placebo carrier material was prepared to contain aspartame as described above in Example 4. A 100 ml solution was prepared to contain 0.5 g chlorpheniramine maleate, 7.5 g pseudoephedrine HCl, 0.19 g methylparaben, 0.063 g propylparaben, 0.1 g menthol, 0.1 ml eucalyptus oil, 0.2 ml peppermint oil, 5.0 g PVP-10, 0.35 g magnasweet 136, 0.25 g magnasweet 110, and 0.20 g of citric acid in absolute ethanol. A 0.20 ml aliquot of the resulting ethanol solution was then carefully loaded on the placebo carrier material. The solvent was allowed to evaporate under vacuum for one hour. The resulting dry dosage form dissolves rapidly in water and also in the mouth. Each unit of dosage form contained 15 mg of pseudoephedrine HCl and 1 mg of chlorpheniramine maleate. The total weight of the dosage form was 90 mg.

EXAMPLE 6

Preparation of a Colored Placebo Carrier Matrix Containing A Dye

Gelatin (pharmaceutical grade) (20 g), mannitol (30 g) and FD&C yellow #5 (0.1 ml) were dissolved in 949.9 g water with heating and constant stirring. The resulting solution was transferred carefully into 1 ml size molds. Placebo samples were prepared as described above in Example 1. This produced a network of a yellow colored carrier material that disintegrated rapidly, in 1 to 5 seconds, when taken orally. The method was repeated with several pharmaceutically acceptable water soluble dyes. Each resulted in a dosage form that weighed 50 mg and dissolved in 1 to 5 seconds upon oral administration.

EXAMPLE 7

Preparation of a Placebo Carrier Matrix Containing A Dispersion of Water Insoluble Pigment Gelatin (pharmaceutical grade) (20 g) and mannitol (30 g) were dissolved in 947 g water with heating and constant stirring. 3 g of an 8–10% dispersion or lake of FD&C yellow #5 was added to the solution with constant stirring. The resulting suspension was sonicated until the pigment was uniformly dispersed. The suspension was then transferred carefully into 1 ml size molds. Placebo samples were then prepared from the suspension as described above in Example 1. This produced a network of a yellow colored carrier material that disintegrated rapidly, in 1 to 5 seconds, when taken orally. The method was repeated with several pharmaceutically acceptable water insoluble lake pigments. Each resulted in a placebo sample that weighed 50 mg and dissolved in 1 to 5 seconds upon oral administration.

EXAMPLE 8

Preparation of a Pharmaceutical Dosage form Containing an Active Agent By Post-Loading a Colored Processed Matrix A 100 ml solution was prepared to contain 3.75 g pseudoephedrine HCl, 0.25 g chlorpheniramine maleate, 1.25 g dextromethorphan, 0.50 g sodium saccharin, and 0.10 g of menthol in absolute ethanol. A colored placebo was prepared as described above in Example 6. To this placebo was added 0.20 ml of the solution and the solvent was subsequently allowed to evaporate in a vacuum chamber for one hour. The resulting dry dosage form dissolves rapidly in water and also in the mouth. Each dosage unit weighed 62 mg and contained 7.5 mg of pseudoephedrine HCl, 0.5 mg of chlorpheniramine maleate and 2.5 mg of dextromethorphan. HBr. Several doses of above three drugs were prepared with different flavor systems such as grape, punch, lemon-lime, raspberry and cherry. Each resulted in a unit dosage form that dissolved rapidly in 1 to 5 seconds when taken orally.

EXAMPLE 9

Preparation of a Pharmaceutical Dosage Form Containing an Active Agent By Post-Loading A Processed Matrix A placebo sample was prepared as described above in Example 1. To this placebo sample was added 0.2 ml of a solution prepared to contain 15.0 g meclizine HCl, 0.1 g menthol, 1.25 g aspartame, 0.1 ml raspberry flavor in sufficient 1:1 chloroform:isopropyl alcohol to yield 100 ml. The solvent was then allowed to evaporate in a vacuum chamber for about one hour. The resulting dosage unit contained 25 mg of meclizine. Several doses of meclizine HCl were prepared with different flavor systems such as grape, punch, lemon-lime, raspberry and cherry. Each resulted in a dosage unit that weighed 83 mg and dissolved in 1 to 5 seconds when taken orally.

EXAMPLE 10

Preparation of a Pharmaceutical Dosage Form Containing Haloperidol as an Active Agent A unit dosage was prepared to contain 5 mg of haloperidol by the method described above in Example 9. A 100 ml chloroform:isopropyl alcohol solution was prepared to contain 2.5 g of haloperidol prior to treating the placebo sample. The resulting dosage forms weighed 61 mg.

EXAMPLE 11

Preparation of a Pharmaceutical Dosage Form Containing Haloperidol as an Active Agent A placebo carrier material was prepared to contain aspartame as described above in Example 4. A 100 ml solution was prepared to contain 2.5 g haloperidol, 0.35 g magnasweet 136, 0.25 g magnasweet 110, 0.5 ml lemon flavor, 0.25 ml orange flavor, and 0.6 g citric acid in warm absolute ethanol. A 0.20 ml aliquot of the resulting ethanol solution was then carefully loaded on the placebo carrier material. The solvent was allowed to evaporate under vacuum for one hour. Each unit of dosage form contains 5 mg of haloperidol.

EXAMPLE 12

Preparation of a Pharmaceutical Dosage Form By Post Loading a Placebo with a Suspension of Active Agent A mixture was prepared to contain 2.0 g albuterol sulfate, 0.1 g menthol, 0.2 g sodium saccharin, and sufficient absolute ethanol to make 100 ml of mixture. After stirring this mixture, it was sonicated until the albuterol sulfate was uniformly dispersed, and 0.2 ml aliquots of the resulting suspension were carefully added to placebo samples prepared as described above in Example 1. Each resulting dosage unit weighed 55 mg and contained 4 mg of albuterol sulfate.

EXAMPLE 13

Preparation of a Unit Dosage Form of Dimenhydrinate by Post-Loading a Processed Matrix with A Suspension of Dimenhydrinate A 100 ml solution was prepared to contain 25 g dimenhydrinate in absolute ethanol. A 0.2 ml aliquot of this solution was then added to placebo units prepared as described in Example 1. Each resulting dosage unit weighed 100 mg, contained 50 mg of dimenhydrinate, and dissolved rapidly in the mouth.

EXAMPLE 14

Preparation of a Breath Freshener Formulation

A 100 ml absolute ethanol solution was prepared to contain 0.19 g methylparaben, 0.063 g propylparaben, 0.1 g menthol, 0.1 ml eucalyptus oil, 0.2 ml peppermint oil, 5.0 g polyvinylpyrrolidone (PVP), 0.25 g magnasweet 110, 0.35 g magnasweet 136, and 0.20 g citric acid. A 0.20 ml aliquot of the resulting solution was then added to placebo samples prepared as described in Example 1. The ethanol was allowed to evaporate under vacuum for one hour. The resulting dry formulations weighed 63 mg and dissolved rapidly in water and also in the mouth.

EXAMPLE 15

Preparation of a Unit Dose of a Low Calorie Sugar Substitute By Solid-State Dissolution Gelatin (pharmaceutical grade) (20.0 g), mannitol (30 g), and aspartame (20.0 g) were dissolved in 930 g of water with heating and constant stirring. The resulting solution was transferred accurately into 1 ml size molds and solidified. The solid-state dissolution procedure was performed as described in Example 1. This produced a network of the carrier material that weighed 60 mg and disintegrated rapidly, in 1 to 5 seconds, when added to a glass of water. The water was found to be considerably sweet in taste.

EXAMPLE 16

Preparation of Rapidly Dissolving Unit Dose Of Buffer By Solid-State Dissolution Gelatin (pharmaceutical grade) (20.0 g), monobasic sodium phosphate (40.0 g), and dibasic sodium phosphate (30.0 g) were dissolved in 910 g water with heating and constant stirring. Solid-state dissolution was performed as described in Example 1 and produced a buffer salt carrier system. Each resulting buffer product weighed 90 mg and disintegrated instantaneously when added to water to produce a solution having the desired specific pH and buffer strength.

EXAMPLE 17

Preparation of a Unit Dry Emulsion By Solid-State Dissolution

Gelatin (pharmaceutical grade) (25.0 g), mannitol (30.0 g) and aspartame (5.0 g) were dissolved in 870 g water with heating and constant stirring and the mixture subsequently was maintained at 60° C. A proprietary triglyceride mixture (70.0 g) and glycerol monostearate (10 g) were melted together at 60° C. and the molten fatty mixture was added to the aqueous gelatin solution at 60° C. with vigorous stirring. The resulting emulsion was cooled and poured into molds. The solid-state dissolution method of Example 1 was followed to produce dry emulsions weighing 140 mg.

EXAMPLE 18

Preparation of a Unit Dosage of a Foam By Solid-State Dissolution

An aqueous solution was prepared to contain 4% by weight gelatin (pharmaceutical grade) and 3% mannitol. To this solution was added 1% sodium diethylsulfosuccinate as a surfactant. Air bubbles were incorporated into the solution by use of a Silverson homogenizer. All of the air bubbles incorporated into the solution were of relatively uniform size and had an average diameter of approximately 100 microns. The resulting solution was then dispensed dropwise into a flask containing liquid nitrogen. The spheres floated not only during freezing, but also continued to float once completely frozen. The frozen spheres were collected and immersed in a bath of absolute ethanol at −15° C. The spheres were removed from the ethanol when the ice had completely dissolved into the ethanol solution. The spheres were subsequently placed in a vacuum oven to remove residual ethanol. The resulting processed spheres weighed 50 mg and dissolved rapidly in 1 to 5 seconds, when taken orally.

EXAMPLE 19

Preparation of a Placebo Carrier Matrix by Solid-State Dissolution

Pectin (5 g), mannitol (50 g), and aspartame (5 g) were dissolved in 940 g of water. The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at −15° C. Each frozen sample weighed 1.00 g. When all the frozen water was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 20

Preparation of a Placebo Carrier Matrix By Solid-State Dissolution

Pectin (20 g) was dissolved in 980 g of water by heating with constant stirring in a boiling hot water bath for periods of 15 min to four hrs. The resulting solution was then allowed to attain room temperature. To 250 g of this solution, 50 g of mannitol, 5 g of aspartame, and 695 g of water were added with constant stirring. The mixture was stirred until mannitol and aspartame dissolved completely.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at −15° C. Each frozen sample weighed 1.00 g. When all the ice was dissolved into the ethanol (5 hours), the product was transferred to a vacuum chamber in order to remove residual ethanol. This produced a sample, i.e. a network of carrier material, that disintegrated rapidly in 1 to 5 seconds when taken orally. Each of the processed samples weighed 50 mg.

EXAMPLE 21

Preparation of a Placebo Carrier Matrix By Solid-State Dissolution

Pectin (20 g) was dissolved in 980 g of water. The resulting solution was autoclaved at 121° C. for 15 minutes. The autoclaved solution was then allowed to attain room temperature. To 500 g of autoclaved solution, 50 g of mannitol, 5 g of aspartame, and 445 g of water were added with constant stirring. The mixture was stirred until mannitol and aspartame dissolved completely.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighted and immersed into 5000 g of absolute ethanol at −15° C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 22

Preparation of a Breath Freshener Formulation

A 100 ml absolute ethanol solution was prepared to contain 0.19 g methylparaben, 0.063 g propylparaben, 0.1 g menthol, 0.1 ml eucalyptus oil, 0.2 ml peppermint oil, 5.0 g polyvinylpyrrolidone (PVP), 0.25 g magnasweet 110, 0.35 g magnasweet 136, and 0.20 g. citric acid. A 0.20 ml aliquot of the resulting solution was then added to placebo samples prepared as described in Example 19. The ethanol was allowed to evaporate under vacuum for one hour. The resulting dry formulations weighed 63 mg and dissolved rapidly in water and also in the mouth.

EXAMPLE 23

Preparation of a Placebo Carrier Matrix By Solid-State Dissolution

Pectin (8 g), microcrystalline cellulose (0.5 g), mannitol (35 g), and aspartame (5 g) were dissolved in 957.5 g of water.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at −15° C. Each frozen sample weighed 1.00 g. When all the ice was dissolved into the ethanol (5 hours), the product was transferred to a vacuum chamber in order to remove residual ethanol. This produced a sample, i.e. a network of carrier material, that disintegrated rapidly in 1 to 5 seconds when taken orally. Each of the processed samples weighted 35 mg.

EXAMPLE 24

Preparation of a Placebo Carrier Matrix By Solid-State Dissolution

Pectin (8 g), sodium starch glycolate (0.5 g), mannitol (35 g), and aspartame (5 g) were dissolved in 957.5 g of water.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighted and immersed into 5000 g of absolute ethanol at −15° C. Each frozen sample weighed 1.00 g. When all the ice was dissolved into the ethanol (5 hours), the product was transferred to a vacuum chamber in order to remove residual ethanol. This produced a sample, i.e., network of carrier material, that disintegrated rapidly in 1 to 5 seconds when taken orally. Each of the processed samples weighed 36 mg.

EXAMPLE 25

Preparation of a Placebo Carrier Matrix By Solid-State Dissolution

Maltrin M100 (Maltodextrin DE10) (100 g), mannitol (30 g), and xanthan gum (0.5 g) were dissolved in 869.5 g of water.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at −15° C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 26

Preparation of a Placebo Carrier Matrix By Solid-State Dissolution

A 10% polydextrose solution (100 g), mannitol (35 g), and aspartame (5 g) were dissolved in 860 g of water with heating and constant stirring.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at $-15°$ C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 27

Preparation of a Placebo Carrier Matrix By Solid-State Dissolution

Locust bean gum (2 g), mannitol (35 g), and aspartame (5 g) were dissolved in 958 g of water with heating and constant stirring.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at $-15°$ C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 28

Preparation of a Placebo Carrier Matrix By Solid-State Dissolution

Carrageenan (5 g) and mannitol (35 g) were dissolved in 960 g of water with heating and constant stirring.

The resulting solution was carefully transferred into 1 ml size molds. A mold consisted of a polyvinyl chloride (p.v.c.) wheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at $-15°$ C. Each frozen sample weighed 1.00 g. When all the ice was dissolved into the ethanol (5 hours), the product was transferred to a vacuum chamber in order to remove residual ethanol. This produced a sample, i.e., a network of carrier material. Each of the processed samples weighed 50 mg.

EXAMPLE 29

Preparation of a Placebo Carrier Matrix By Solid-State Dissolution

Konjac flour (5 g), mannitol (35 g), and aspartame (5 g) were added to 955 g of water with heating and constant stirring.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at $-15°$ C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 30

Preparation of a Placebo Carrier Matrix By Solid-State Dissolution

Hydroxyethylcellulose (5 g), mannitol (50 g), and aspartame (5 g) were dissolved in 940 g of water with heating and constant stirring.

The resulting solution was carefully transferred into 1 ml size molds. A mold consisted of a polyvinyl chloride (p.v.c.) sheet with 50 cylindrical depressions (18 mm diam. and 5 mm deep). The p.v.c. sheet and its contents were cooled with dry ice for about one hour or frozen quickly in a cold gas freezing tunnel. The frozen contents were weighed and immersed into 5000 g of absolute ethanol at $-15°$ C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 31

Preparation of a Placebo Carrier Matrix by Solid-State Dissolution Using a Dynamic Flow Through System Gelatin (pharmaceutical grade, 20 g) and mannitol (30 g) were dissolved in 950 g of water. The resulting solution was carefully transferred into 1 ml size molds. A mold consisted of a polyvinyl chloride (p.v.c.) sheet with cylindrical depressions (18 mm diameter and 5 mm deep).

The p.v.c. sheet with its contents was cooled with dry ice for about one hour, or alternatively quickly solidified·in a cold gas freeze tunnel. The frozen contents were weighed and stored at $-15°$ C. Each frozen sample weighed 1.00 g.

The flow through system consisted of the following:
1. Primary Reservoir: It consisted of an airtight container of suitable size that contained open shelved compartments. It served as a reservoir for frozen tablets during the solid-state dissolution procedure. It also contained an air diffuser assembly at the bottom of the container.
2. Secondary Reservoir: It consisted of an airtight container of suitable size, which served as a reservoir for ethanol. The ratio of primary to secondary reservoir size was about 6:1.

3. Pump and Tubing: The two reservoirs were connected to the pump via suitable tubing in a closed system.

The primary and secondary reservoirs were maintained at −15° C. The solidified tablets were placed in the primary reservoir compartments in one to six tablet layer thicknesses. About 5,000 g of absolute ethanol were transferred from the secondary reservoir into the primary reservoir. About 1,000 g of absolute ethanol were pumped into the secondary reservoir. Ethanol was circulated from the secondary to the primary reservoir and back to the secondary reservoir at the rate of 0.03 l/min to 2 l/min in a closed system. Every one or two hours, the circulating ethanol was replaced with fresh absolute ethanol. Four to five batches of fresh absolute ethanol over a period of five to eight hours were found to be adequate to dissolve all the frozen water. When all the ice was dissolved into ethanol and the ethanol drained, the primary reservoir was connected from the bottom to a supply of dry air. The dry air was blown through the air diffuser system into the product until the product was completely dry. This produces a sample, i.e., a network of carrier material, that disintegrated rapidly in one to five seconds when taken orally. Each of the processed samples weighed 50 mg.

EXAMPLE 32

Preparation of a Placebo Carrier matrix by Solid-State Dissolution Using a Dynamic Flow Through System Gelatin (pharmaceutical grade, 20 g) and mannitol (30 g) were dissolved in 950 g of water. The resulting solution was carefully transferred into 1 ml size molds. A mold consisted of a polyvinyl chloride (p.v.c.) sheet with cylindrical depressions (18 mm diameter and 5 mm deep).

The p.v.c. sheet, with its contents, was cooled with dry ice for about one hour, or alternatively, quickly solidified in a cold gas freeze tunnel. The frozen contents were weighed and stored at −15° C. Each frozen sample weighed 1.00 g.

The flow through system consisted of the following:
1. Reservoir: It consisted of an airtight container of suitable size, which contained open shelved compartments. It served as a reservoir for frozen tablets during the solid-state dissolution procedure. It also contained an air diffuser assembly at the bottom of the container.
2. Pump and Tubing: The reservoir was connected to the pump via suitable tubing in a closed system.

The reservoir was maintained at −15° C. The solidified tablets were placed in the reservoir in one to six tablet layer thicknesses. About 5,000 g of absolute ethanol were filled into the reservoir. The ethanol was circulated from the top to the bottom of the reservoir at the rate of 0.03 l/min in a closed system. At one or two hour intervals, the system was replaced with fresh absolute ethanol. About four to five batches of fresh absolute ethanol were found to be adequate to dissolve all the ice. When all the ice was dissolved into ethanol, the reservoir (after draining ethanol) was connected from the bottom to a supply of dry air. The dry air was blown through the air diffuser system into the product until the product was completely dry. This produced a sample, i.e., a network of carrier material, that disintegrated rapidly in one to five seconds when taken orally. Each of the processed samples weighed 50 mg.

EXAMPLE 33

Preparation of a Placebo Carrier Matrix By Solid-State Dissolution Using a Dynamic Flow Through System Gelatin (pharmaceutical grade, 20 g) and mannitol (30 g) were dissolved in 950 g of water. The resulting solution was carefully transferred into 1 ml size molds. A mold consisted of a polyvinyl chloride (p.v.c.) sheet with cylindrical depressions (18 mm diameter and 5 mm deep).

The p.v.c. sheet, with its contents, was cooled with dry ice for about one hour, or alternatively, quickly solidified in a cold gas freeze tunnel. The frozen contents were weighed and stored at −15° C. Each frozen sample weighted 1.00 g.

The flow through system consisted of the following:
1. Reservoir: It consisted of an airtight container of suitable size, which contained open shelved compartments. It served as a reservoir for frozen tablets during the solid-state dissolution procedure. It also contained an air diffuser assembly at the bottom of the container.
2. Mixing device: It consisted of suitable mixing apparatus, such as propeller/shaft type stirrer or magnetic stir bar/stir plate. The mixing device was used to provide a homogenous solvent/water mixture.

The reservoir was maintained at −15° C. The solidified tablets were placed in the reservoir in one to six tablet layer thicknesses. About 5,000 g of absolute ethanol were filled into the reservoir. The ethanol was agitated by a suitable mixing device.

At one or two hour intervals, the system was replaced with fresh absolute ethanol. About four to five batches of fresh absolute ethanol changes were found to be adequate to dissolve all the ice. When all the ice was dissolved into ethanol, the reservoir (after draining ethanol) was connected from the bottom to a supply of dry air. The dry air was blown through the air diffuser system into the product until the product was completely dry. This produced a sample, i.e., a network of carrier material, that disintegrated rapidly in one to five seconds when taken orally. Each of the processed samples weighted 50 mg.

EXAMPLE 34

Preparation of a Placebo Carrier Matrix By Solid-State Dissolution

Pectin (20 g) was dissolved in 980 g of water. The resulting solution was autoclaved at 121° C. for 15 minutes. The autoclaved solution was then allowed to attain room temperature. To 425 g of the autoclaved solution, 10 g of mannitol, 2.5 g of aspartame, 50 g of glycine and 512.5 g of water was added with constant stirring. The mixture was stirred until mannitol and aspartame dissolved completely.

The resulting solution was carefully transferred into 1 ml size molds. A mold consisted of a polyvinyl chloride (p.v.c.) sheet with 50 cylindrical depressions (18 mm diameters and 5 mm deep). The p.v.c. sheet and its contents were cooled with dry ice for about one hour. At the end of one hour the frozen contents were weighed and immersed into 5000 g of absolute ethanol at −15° C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 70 mg.

EXAMPLE 35

Preparation of a Placebo Carrier Matrix by Solid-State Dissolution

Gelatin (pharmaceutical grade) (20 g), glycine (30 g), and aspartame (2.5 g) were dissolved in 940 g of water. The resulting solution was carefully transferred into 1 ml size molds. A mold consisted of a polyvinyl chloride (p.v.c.) sheet with 50 cylindrical depressions (18 mm diameter and 5 mm deep). The p.v.c. sheet and its contents were cooled with dry ice for about one hour. At the end of one hour, the frozen contents were weighed and immersed into 5000 g of absolute ethanol at −15° C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

EXAMPLE 36

Preparation of a Placebo Carrier Matrix by Solid-State Dissolution

Gelatin (pharmaceutical grade) (20 g), glycine (50 g), and aspartame (2.5 g) were dissolved in 940 of water. The resulting solution was carefully transferred into 1 ml size molds. A mold consisted of a polyvinyl chloride (p.v.c.) sheet with 50 cylindrical depressions (18 mm diameter and 5 mm deep). The p.v.c. sheet and its contents were cooled with dry ice for about one hour. At the end of one hour, the frozen contents were weighed and immersed into 5000 g of absolute ethanol at −15° C. Each frozen sample weighed 1.00 g. When all the ice was dissolved into the ethanol (5 hours), the product was transferred to a vacuum chamber in order to remove residual ethanol. This produced a sample, i.e., a network of carrier material, that disintegrated rapidly in 1 to 5 seconds when taken orally. Each of the processed samples weighed 50 mg.

From the foregoing it will be appreciated that, although specific embodiments of the invention have been described herein for purposes of illustration, various modifications may be made without deviating from the spirit and scope of the invention.

We claim as my invention:

1. A method for preparing a porous delivery matrix comprising the steps of:
   (a) solidifying a dispersion or solution of a matrix forming agent in a first solvent;
   (b) contacting the solidified dispersion or solution with a second solvent, the first solvent in the solidified dispersion or solution being substantially miscible with the second solvent, the solidification point of the first solvent being higher than the solidification point of the second solvent, the second solvent being at a temperature at or higher than the solidification point of the second solvent and at a temperature at or lower than the solidification point of the first solvent, the matrix forming agent being substantially insoluble in the second solvent, the contacting being sufficient to substantially remove the first solvent from the solidifed disperison or solution thereby yielding a delivery matrix that is substantially free of the solvent; and
   (c) recovering the delivery matrix.

2. The method according to claim 1, comprising the additional step of:
   (d) evaporating residual second solvent from the delivery matrix.

3. The method according to claim 1, comprising the additional step of:
   (d) removing residual second solvent from the delivery matrix by contacting the matrix with one or more additional solvents having greater volatility than the second solvent.

4. The method according to claim 1, wherein the matrix forming agent is selected from the group consisting of gelatins, dextrins, soy proteins, wheat proteins, psyllium seed proteins, gums, alginates, polysaccharides, carboxymethylcellulose, carrageenans, dextrans, pectins, polyvinylpyrrolidone, gelatin-acacia complexes, mannitol, dextrose, lactose, galactose, cyclodextrin, konjac flour, cellulose, sodium starch glycolate, polydextrose, hydroxyethylcellulose, amino acids having 2 to 12 carbon atoms, corn syrup solids, chitosan, rice flour, wheat gluten, soy fiber proteins, potato proteins, papain, horse radish peroxidase and mixtures thereof.

5. The method according to claim 4, wherein at least one of the matrix forming agents is selected from the group consisting of gelatin, pectin, mannitol and glycine.

6. The method according to claim 4, wherein the matrix forming agent is present in a concentration of about 0.1 to 15% by weight of the dispersion or solution.

7. The method according to claim 1, wherein the second solvent is at a temperature from about 1° to 100° C. lower than solidification point of the first solvent.

8. The method according to claim 1, wherein the second solvent to total delivery matrix weight ratio is from about 2:1 to about 40:1.

9. The method according to claim 1, wherein the dispersion or solution also contains an active agent to be delivered, the active agent being substantially insoluble in the second solvent.

10. The method according to claim 1, comprising the additional step of:
    (c) contacting the delivery matrix with an active agent to be delivered such that the active agent is dispersed through the matrix.

11. A method for preparing a porous foam dosage form comprising the steps of:
    (a) forming a dispersion of a gas and a matrix forming agent in a first solvent;
    (b) maintaining the gas in a dispersed state within said dispersion;
    (c) solidifying the dispersion;
    (d) contacting the solidified dispersion with a second solvent, the first solvent in the solidified dispersion being substantially miscible with the second solvent, the solidification point of the first solvent being higher than the solidification point of the second solvent, the second solvent being at a temperature at or higher than the solidification point of the second solvent and at a temperature at or lower than the solidification point of the first solvent, the matrix forming agent being substantially insoluble in the second solvent, the contacting being sufficient to substantially remove the first solvent from the solidified dispersion thereby yielding a foam dosage form; and (e) recovering the foam dosage form.

12. The method according to claim 11, comprising the additional step of:

(f) contacting the foam dosage form with an active agent, such that the active agent is dispersed through the dosage form.

13. The method according to claim 11 wherein the dispersion further comprises an active agent.

14. The method according to claim 1 wherein the delivery matrix additionally comprises an active agent.

15. The method according to claim 11 wherein the foam dosage form additionally comprises an active agent.

* * * * *